United States Patent
Yao

[11] Patent Number: 5,564,424
[45] Date of Patent: Oct. 15, 1996

[54] METHOD AND APPARATUS FOR PULSED DOPPLER ULTRASOUND BEAM-FORMING

[75] Inventor: Lin-Xin Yao, Bellevue, Wash.

[73] Assignee: Siemens Medical Systems, Inc., Iselin, N.J.

[21] Appl. No.: 497,061

[22] Filed: Jun. 30, 1995

[51] Int. Cl.⁶ .................................................. A61B 8/06
[52] U.S. Cl. .................................................. 128/661.09
[58] Field of Search ............. 128/660.05, 661.07–661.1

[56] References Cited

U.S. PATENT DOCUMENTS

| | | | |
|---|---|---|---|
| 4,830,015 | 5/1989 | Okazaki | 128/660.04 X |
| 5,355,888 | 10/1994 | Kendall | 128/660.07 |
| 5,357,964 | 10/1994 | Spivey et al. | 128/661.09 |
| 5,398,216 | 3/1995 | Hall et al. | 128/661.08 X |
| 5,409,010 | 4/1995 | Beach et al. | 128/661.09 |
| 5,421,333 | 6/1995 | Takamizawa et al. | 128/661.01 |
| 5,441,052 | 8/1995 | Miyajima | 128/661.09 |
| 5,454,372 | 10/1995 | Banjamin et al. | 128/661.08 |

Primary Examiner—Francis Jaworski

[57] ABSTRACT

This invention addresses the aliasing and range ambiguity artifact trade-off occurring in pulsed doppler ultrasound applications. By increasing pulse repetition frequency to avoid aliasing and by implementing non-coinciding transmit and receive beam-patterns, range ambiguity effects are reduced. Separate transmit and receive apertures define respective transmit and receive beam-patterns. These separate transmit and receive beam-patterns intersect at a primary range gate. Secondary range gates may occur along the receive beam-pattern. The transmit beam-pattern does not intersect such secondary gates. Weaker dispersed ultrasound energy may intersect the secondary gates, however, and reflect back to the receive aperture. Relatively stronger samples are obtained from the primary range gate than from the secondary range gates. In effect the geometry of the transmit and receive beam-patterns maximizes the strength of the response from the primary gate and reduces the strength of the response from the secondary gates.

3 Claims, 4 Drawing Sheets

METHOD AND APPARATUS FOR PULSED DOPPLER ULTRASOUND BEAM-FORMING

BACKGROUND OF THE INVENTION

This invention relates generally to medical diagnostic ultrasound systems and more particularly to high-PRF pulsed-doppler ultrasound methods and apparatus.

Sound waves having a frequency greater than approximately 20 kHz are referred to as ultrasound. In medical diagnostic applications, ultrasound signals are transmitted into a patient's body where they are in-part absorbed, dispersed, refracted and reflected. Reflected ultrasound signals are received at transducer elements which convert the reflected ultrasound signals back into electronic signals.

A final ultrasound beam-pattern, to the first order, is a product of a transmit beam-pattern and a receive beam-pattern. The final beam-pattern typically is processed to analyze echo, doppler and flow information and obtain an image of the patient's encountered anatomy (e.g., tissue, flow, doppler). Diagnostic sonography refers to the medical cross-sectional anatomic and flow imaging derived from pulse-echo ultrasound signals. Doppler ultrasound is the field of detection, quantization, and medical evaluation of tissue motion and blood flow. Continuous wave doppler ultrasound (i.e., cw-doppler) uses continuous-wave ultrasound signals. Pulsed doppler ultrasound uses pulsed-wave ultrasound signals.

This invention relates to pulsed-wave doppler ultrasound. Applications of doppler ultrasound are found in virtually all medical specialties, including cardiology, neurology, radiology, obstetrics, pediatrics and surgery. Flow can be detected even in vessels that are too small for sonographic imaging. Doppler ultrasound is used to determine the presence or absence of flow, the direction and speed of flow, and the character of flow. Doppler instruments typically provide both audible and visual outputs indicative of blood flow information. CW-doppler instruments are used to monitor a large sample volume, but can give complicated and confusing presentations if reflectors or scatterers with different motions or flows are included in the volume. Pulsed doppler systems address this difficulty by detecting motion or flow at selected depths within a relatively small volume (i.e., a range gate).

Doppler ultrasound is based upon the doppler effect, which is a change in frequency caused by the relative motion among a wave source, receiver and reflector. As applied to medical applications, an ultrasound transducer embodying the source and receiver is stationary, while blood or tissue fluid is the moving reflector. The change in frequency detected is the difference between the transmitted ultrasound signal frequency and the reflected ultrasound signal frequency. Such change is a function of the transmitted signal frequency, the propagation speed of the transmitted signal through the patient's anatomy, the speed of flow in the range gate and the angle of incidence between the ultrasound signal and the direction of blood flow.

Pulsed doppler ultrasound instruments emit ultrasound pulses and receives echoes using typically a single element or array transducer. Using range gating, pulsed doppler provides the ability to select information from a particular location (e.g., depth) within the anatomy along the beam. Typically pulsed doppler is combined with real-time sonography imaging for medical diagnostic applications.

A pulsed doppler instrument includes a voltage generator (e.g., oscillator) with an oscillator gate that generates electrical signal inputs to a transducer. The oscillator gate allows respective pulses of several voltage cycles to pass to the transducer for conversion into respective ultrasound pulses. Ultrasound pulses used for doppler have minimum pulse lengths of approximately five cycles and typical pulse lengths of 25–30 cycles. The multiple cycles within a pulse are used to determine the doppler shift of returning echoes. Voltage pulses resulting from received echoes are processed in a receiver, where they are amplified and compared in frequency with the transmitted signal. Also, a doppler shift is derived and sent to loudspeakers and a visual display.

A range gate is defined for selecting the echoes corresponding to a given depth. Specifically, a sample volume is defined as the range gate. Echoes arrive from the sample volume at a rate determined by a pulse repetition frequency ("PRF"), (i.e., number of pulses transmitted per second). Each of these returning echoes yields a sample of the Doppler shift. The samples are processed, connected and filtered to derive a sample waveform. The range gate selects a listening region from which the returning echoes are accepted. The width and height of the range gate is determined by the width and height of the beam. The length of the range gate is determined by the pulse length, (i.e., one half the pulse length is added to the gate length to yield a sample volume length). Larger range gate lengths (e.g., 10 mm) are used when searching for a desired vessel or flow location. Shorter lengths (e.g., approximately 2 mm) are used for spectral analysis and evaluation. The shorter range gate length improves signal-to-noise ratio and the quality of a spectral trace. A single range gate permits only one depth and length selection at a given time.

The echoes sensed at a range gate undergo spectral analysis of frequency components. Typically, several frequency components are present. If all flow within the range gate were of a uniform speed and direction, then there would only be one frequency component. The character of flow in vessels, however, is determined by the vessel size and the uniformity of its walls. Changes in size, turns and abnormalities, such as the presence of plaques and stenoses, alter the character of the flow. Conventionally, flow is characterized as plug, laminar, parabolic, disturbed, and turbulent. Accordingly, portions of flow often are moving at different speeds and, sometimes, in different directions. Thus, many different doppler shifts, and thus frequency components, occur. Typically, the doppler response undergoes fast Fourier transform analysis to derive the component frequencies.

In certain instances, artifacts occur in doppler ultrasound. Artifacts as used herein are anything that is not properly indicative of the structures of the flows imaged or sampled. More specifically, artifacts are incorrect presentations of flow or image information. Artifacts are caused by some characteristic of the sampling or imaging technique. Although other imaging and doppler artifacts occur, addressed here are two common doppler ultrasound artifacts—aliasing and range ambiguity.

Aliasing is the improper representation of information that has been insufficiently sampled. The sampling can be of a spatial or temporal nature. As the sampling rate is reduced, for example, the ability to resolve the details of an object, then the general character of the object, is lost. In cases this results in the object being mis-characterized (e.g., having a false appearance or assumed identity—an alias). An example of temporal aliasing occurs in, for example, a rotating object such as a fan. The blades of the fan are observed to rotate at various speeds and in reverse directions when viewed with a strobe light flashing at various rates.

The Nyquist limit or Nyquist frequency describes the minimum sampling rate required to avoid aliasing. Specifically, there must be at least two samples per period of the wave being observed. For a complicated signal, such as a doppler echo signal containing many frequencies, it is preferable that the sampling rate be sufficient to include at least two samples for each period of the highest doppler-shift frequency present. Stated differently, if the highest doppler-shift frequency present in a signal exceeds one half the pulse repetition frequency, then aliasing occurs. On a doppler spectral display, frequency aliasing is manifested as a "wrapping around" of the spectrum so that blood of high velocity in one direction instead appears to be going in the opposite direction. To reduce aliasing, the pulse repetition frequency (PRF) often is increased.

The range ambiguity artifact often is encountered in attempting to solve the aliasing problem, (e.g., when increasing the PRF). Range ambiguity occurs when a pulse is emitted before all the echoes from the preceding pulse have returned. In such cases, the late echoes from the prior pulse are received contemporaneously with early echoes from a current pulse. As a result, the doppler instrument is unable to determine whether the echo is an early echo from the current pulse or a late echo from the previous pulse. Typically, the instrument assumes that all echoes are derived from the current pulse—and attributes a corresponding depth to each respective echo. For high pulse repetition frequencies, such assumption is invalid. In such instances Doppler information is coming from locations other than the sample volume (i.e., the gate location). In effect, multiple gates are occurring at different depths. The multiple range gates are referred to as a real or primary range gate and one or more phantom or secondary range gates. The primary range gate is the sample volume of interest. The phantom range gates create range ambiguity.

In countering the aliasing and range ambiguity artifacts, one desires to increase the pulse repetition frequency to avoid aliasing, but not increase it so much that range ambiguity occurs. In practice, frequency aliasing sets a lower bound for the pulse repetition frequency, while range ambiguity sets an upper bound. Equation I defines the aliasing bound. Equation II defines the range ambiguity bound.

$$f_R > 2 f_{Dmax} \quad (I)$$

$$f_R < c/2d_{max} \quad (II)$$

Where $f_R$=pulse repetition frequency;

$f_{Dmax}$=highest doppler shift that might be encountered;

c=propagation speed of ultrasound in tissue; and $d_{max}$=maximum depth for receiving echoes.

Resolving equations I and II gives:

$$f_{Dmax} * d_{max} < c/4 \quad (III)$$

When equation III is true, pulsed doppler is effective to avoid aliasing and range ambiguity. Unfortunately, neither $f_{Dmax}$ nor $d_{max}$ are known in advance. When nature is not cooperative, a compromise solution typically is adopted. In practice, one either (a) uses a high pulsed repetition mode in which multiple gates are observed, or (b) uses cw-doppler where range discrimination is completely sacrificed in the interest of avoiding frequency aliasing. This invention is directed toward the first alternative—use of a high PRF. The term high-PRF pulsed-doppler as used in this application refers to doppler ultrasound signals which do not conform with equation II, (i.e., signals having a pulse repetition frequency, $f_R$, greater than or equal to the range ambiguity bound, $c/2d_{max}$). More specifically, this invention is directed toward avoiding, or reducing the impact of range ambiguity in the presence of phantom gates.

SUMMARY OF THE INVENTION

This invention addresses the aliasing and range ambiguity artifact trade-off often occurring in pulsed-doppler, medical-diagnostic, ultrasound applications. Specifically, in the past one has traded-off range ambiguity to avoid aliasing. The aliasing and range ambiguity problems are described above in the background section. According to the solution of this invention, phantom or secondary range gates are permitted. The method and apparatus of this invention, however, minimizes the effects of the phantom or secondary range gates allowing the echoes from the primary gate to dominate the measured response. Thus, range ambiguity is avoided, or at least reduced, even though multiple gates occur.

According to the invention, separate transmit and receive apertures define respective transmit and receive beam-patterns. These separate transmit and receive beam-patterns are not aligned. For conventional doppler ultrasound instruments, the same transducer is time-shared to serve as a transmitter and receiver resulting in (i) an overlapping transmit and receive aperture and (ii) a generally coincident transmit beam-pattern and receive beam-pattern. The final beam pattern is the product of the transmit and receive beam-patterns. The presence of phantom or secondary gates along a coincident beam-pattern yields undesirable range ambiguity. By having separate apertures producing non-aligned, non-coincident beam-patterns per this invention, only one area of intersection occurs between the transmit and receive beam-patterns. Instead of the beam-patterns being intersecting along the entire pattern, only one area, or more specifically volume, defines the intersection.

According to one aspect of this invention, the transmit and receive beam-patterns are focussed and crossed at a target sample-depth. Such target sample-depth is the primary range gate, (i.e., the sample volume). By intersecting the beams at the target, the maximum useful signal is collected from the target. Further, by intersecting at the primary range gate, the transmit beam does not pass through the exact locations of any phantom (secondary) range gates. Thus, the strength of the phantom range gate echoes are substantially reduced. In effect, the geometry of the transmit and receive beam-patterns maximizes the strength of the response from the primary gate and reduces the response from the phantom (secondary) gate(s).

One advantage of the invention is that sufficiently high pulse repetition frequencies can be used in pulsed doppler ultrasound applications to avoid frequency aliasing without introducing adverse range ambiguity in the final beam-pattern. A beneficial effect is that pulsed doppler can be used effectively over a wider range of applications and deeper sample depths to detect flow patterns.

DETAILED DESCRIPTION

OVERVIEW—PULSED DOPPLER ULTRASOUND SYSTEM

Figure 1:
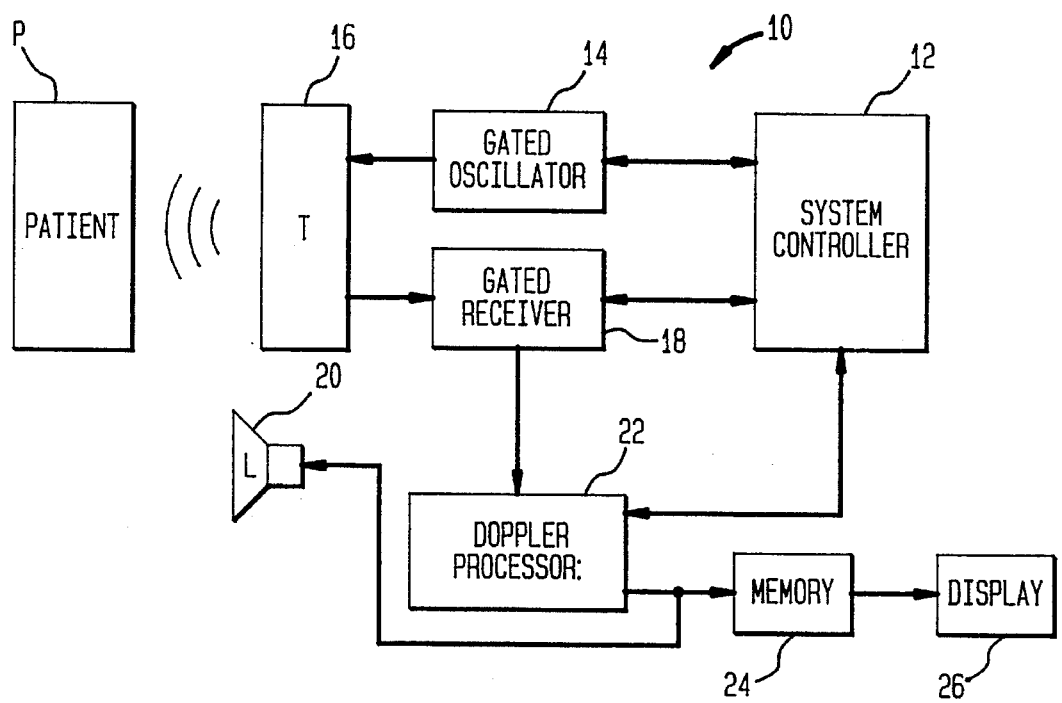
FIG. 1 is a block diagram of a pulsed doppler ultrasound system.

FIG. 1 shows a pulsed doppler ultrasound system 10 used in medical diagnostic applications. The system 10 emits ultrasound pulse wave-forms and detects response echoes to identify motion (e.g., blood flow, fluid motion) within a patient's anatomy. The ultrasound system 10 includes a system controller 12, gated oscillator 14, transducer 16, gated receiver 18, loud-speaker 20, doppler processor 22, memory 24 and display 26. The system controller 12 provides a user interface (e.g., control panel, display menu, keyboard) (not shown) and controls system operations. In operation, the system controller 12 triggers the gated oscillator 14 to generate electrical signals for output to the transducer 116. The transducer converts the electrical signals into a doppler ultrasound transmit pulse wave-pattern. Typically, the transducer is positioned adjacent to and in contact with a patient's anatomy. The transmit pulse wave-pattern propagates into the patient's anatomy where it is refracted, absorbed, dispersed and reflected. The degree of refraction, absorption, dispersion and reflection depends on the uniformity, density and structure of the encountered anatomy. Of interest is the reflected components which propagate back to the transducer 16. These echoes are sensed by the transducer 16 and converted back into electrical signals. The electrical signals are input to a gated receiver which amplifies the signals.

For pulsed doppler a pulse wave-form is transmitted and echoes responsive to the pulse are detected. To define the pulse the oscillator 14 is gated. To sense echo response to the pulse the receiver 18 also is gated. In effect, time windows are defined for transmitting and receiving ultrasound energy.

The converted echo signals are fed to a doppler processor 22. The doppler processor 22 performs spectral analysis of the echoes to define the doppler-shift frequency components of the echoes. The doppler shift information then is used to define flow information which is stored in memory 24 and output to a display device 26. The loudspeaker 20 converts the doppler-shift components (illustrated as signal 88 in FIG. 8) into sound within the human hearing range.

Typically, sonographic imaging subsystems also are included to define an ultrasound system having both doppler capability and sonographic imaging capability. The sonographic subsystems are not shown in FIG. 1.

Figure 2:
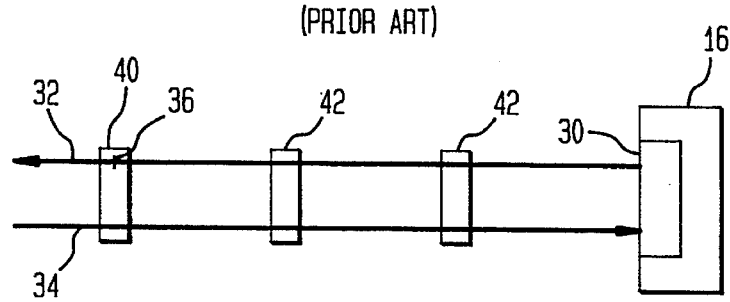
FIG. 2 is a diagram of conventional pulsed doppler transmit and receive apertures in alignment.

Conventional pulsed doppler ultrasound applications use a single transducer array 16 which is time-shared between transmit and receive operations. In addition, physically overlapping transmit and receive apertures 30 are defined at the transducer 16. Accordingly, a transmit pulse wave-pattern 32 is emitted from the transmit aperture 30 during one interval of time, followed by an echo beam-pattern being received at the coinciding receive aperture 30 at a subsequent interval of time. As shown in FIG. 2, the transmit pulse wave-pattern 32 and the receive beam-pattern 34 coincide—(the two patterns 32, 34 are shown adjacent for illustrative purposes, but occur as generally coincident, aligned, overlapping patterns occurring in approximately the same physical space).

By performing pulsed doppler operations, the transmit pulse wave-pattern 32 and receive beam-pattern 34 each can be focussed to a target. Thus, the transmit pulse wave-pattern is focussed at a depth 36 and the receive beam-pattern is focussed at a sample volume 40. Preferably, the depth 36 is within the target sample volume 40. The sample volume 40 has a width and height determined by the receive aperture, and has a length (i.e., depth increment) determined by the gating of the receiver 18. The target sample volume 40 also is referred to as a primary range gate 40. Accordingly, in performing pulsed doppler ultrasound, a primary range gate is defined from which echo signals are sampled.

As described in the background section, however, aliasing and/or range ambiguity artifacts occur when the following equation is not met:

$$f_{Dmax} * d_{max} < c/4 \tag{III}$$

where $f_{Dmax}$=highest doppler shift that might be encountered;

c=propagation speed of ultrasound in tissue; and $d_{max}$=maximum depth for receiving echoes.

Unfortunately, neither $f_{Dmax}$ nor $2d_{max}$ are known in advance. Thus, calculated avoidance of these artifacts can be difficult. In particular, for applications using a relatively high pulse repetition frequency (e.g., frequency not within limits of equation I), estimating avoidance of the artifacts is difficult. As a result, secondary or phantom range gates 42 occur in some applications (e.g., when equation II is not met). FIG. 2 shows the example where the pulse repetition frequency for a transmit pulse wave-pattern is sufficiently high that the echo from the primary range gate 40 responsive to a first pulse of the wave-pattern occurs after a second pulse of the wave-pattern. As a result, early echoes from the second pulse are sensed with the late-arriving first pulse echo from the primary range gate 40. These early echoes in effect define additional secondary range gates 42. As it is the primary range gate that is the target of interest, the secondary range gates 42 introduce range ambiguity.

SEPARATE TRANSMIT AND RECEIVE APERTURES

Figure 3:
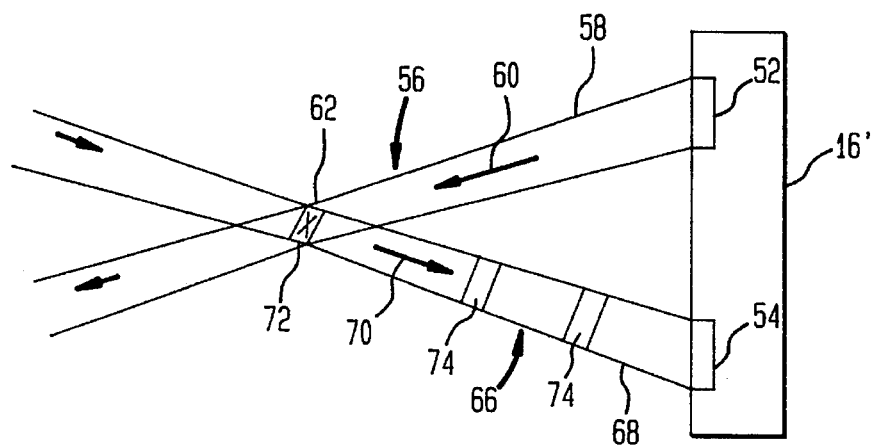
FIG. 3 is a diagram of separate pulsed doppler transmit and receive apertures defining a pulsed doppler beam-pattern having a primary range gate at the intersection of transmit and receive beam-patterns according to one embodiment of this invention.

FIG. 3 shows the inventive solution for the aliasing versus range ambiguity trade-off. Separate apertures 52, 54 are defined by a single or multiple transducers 16'. More significantly, the transmit pulse wave-pattern is oriented to travel a different, non-aligned, non-coincident path than the returning receive beam-pattern.

At given intervals in time, a pulse from the transmit pulse wave-pattern 56 is emitted from aperture 52. The ultrasound energy of the pulse is in part refracted, absorbed, dispersed and reflected. The propagating refracted portions of multiple, sequential pulses generally define the transmit pulse wave-pattern 56. The pattern 56 propagates along a path 58 in a general direction 60. Due to non-uniformity of the patient anatomy encountered, it is expected that portions of each pulse will disperse and scatter along other paths and directions. A general path 58 and direction 60, however, occur where most of the non-absorbed, non-reflected energy propagates. The transmit pulse wave-pattern is focussed at a desired depth 62.

When a transmit pulse is not being output from the aperture 52, a receive aperture 54 and gated receiver 18 gate a receive beam-pattern 66. The receive beam-pattern 66 is formed by echo responses to the transmit pulse wave-pattern reflecting back to the receive aperture 54. The receive beam-pattern 66 travels a path 68 along a general direction 70. Like the transmit pulse, the echoes also are in part absorbed, refracted, dispersed and reflected. A general path 68 and direction 70, however, occur where most of the non-absorbed energy propagates back toward the receive aperture 54. The gated receiver 18 focusses the receive beam-pattern 66 to capture samples from a target sample volume 72. The gating action of the receiver 18 captures echo samples during select time windows.

The sample volume 72 has a width and height determined by the receive aperture 54, and has a length (i.e., depth increment) determined by the gating of the receiver 18. A typical length is 0.5 mm to 20 mm. The target sample volume 72 also is referred to as a primary range gate 72. Accordingly, in performing pulsed doppler ultrasound, a primary range gate 72 is defined from which echo signals are sampled. The primary range gate is defined to occur at the intersection of the transmit pulse wave-pattern 56 and the receive beam-pattern 66.

Like in the conventional configuration of FIG. 2, secondary gates 74 occur along the receive beam-pattern when Equation II is not met. Thus, multiple range gates occur. In the FIG. 2 configuration, however, the transmit pulse wave-pattern 32 intersects the secondary range gates 42. In the inventive configuration, however, the transmit pulse wave-pattern 56 only intersects the primary gate 72. In general, the transmit pulse beam-pattern 56 does not intersect the secondary range gates 74. Only small dispersed energy portions travel within the secondary range gates 74 to be reflected to the receive aperture 54. Thus, the strength and occurrence of the signals sampled in the secondary range gates 74 are less than those in the primary range gate 72. In practice, the primary range gate 72 samples dominate the receive beam-pattern 56 samples. Thus, the range ambiguity is less pronounced, less significant, and easier to dismiss by the doppler processor 22 or the ultrasound operator.

Figure 4:
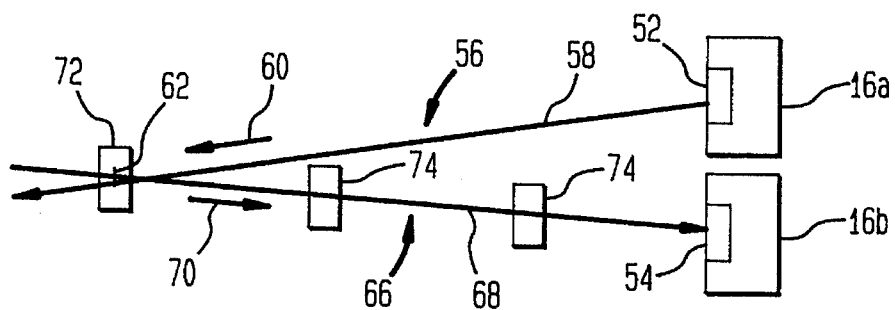
FIG. 4 is a diagram of non-aligned transmit and receive beam-patterns intersecting at a primary range gate according to another embodiment of this invention.
Figure 5:
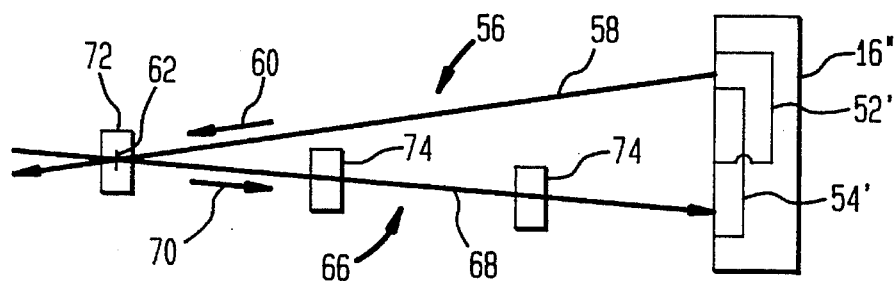
FIG. 5 is a diagram of non-aligned transmit and receive beam-patterns intersecting at a primary range gate according to yet another embodiment of this invention.

FIG. 4 shows an alternate embodiment in which the transmit aperture 52 and receive aperture 54 occur at physically separate transducers 16a, 16b. FIG. 5 shows another alternative embodiment having a transducer array 16" in which the transmit aperture 52' and receive aperture 54' overlap, but remain non-coincident. Accordingly, the transmit apertures occur on a common transducer array 16', 16" or separate transducer arrays 16a, 16b. Further, the transmit and receive apertures may define transducer elements in common (e.g., time-shared transducer elements—see FIG. 5). Accordingly, when the terms first transducer and second transducer are used in the claims, the first transducer and second transducer may be physically distinct transducer elements on separate or a common transducer array; or a combination of distinct transducer elements and one or more time-shared transducer elements on a common (FIG. 5) or separate transducer arrays.

According to various embodiments, the acute angle formed by the beams at the primary range gate is between 5° and 30°, and preferably between 15° and 30°. Also, the acute angle formed between the transmit pulse beam-pattern 56 and the surface of the transducer 16' is between ±45°. Similarly, the acute angle formed between the receive beam-pattern 66 and the surface of the transducer 16' is between ±45°.

HIGH-PRF PULSED-DOPPLER ULTRASOUND METHOD

Figure 6:
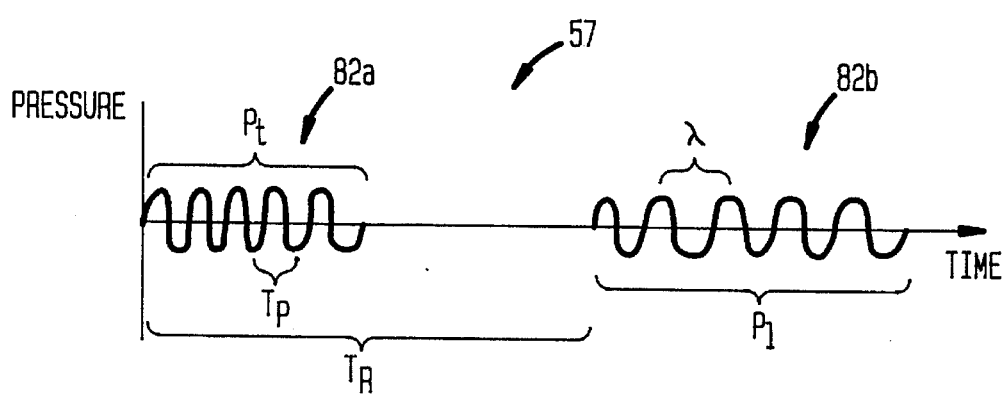
FIG. 6 is a chart of a transmit signal input to a transducer element which generates in response a transmit pulse wave-pattern.

According to the method of this invention, a doppler-ultrasound transmit pulse wave-pattern 56 and receive beam-pattern 66 are non-aligned and non-coincident. The patterns 56, 66 intersect at a primary range gate 72. The doppler ultrasound transmit pulse wave-pattern 56 is generated at a transmit aperture 52. FIG. 6 shows an exemplary transmit signal 57 for generating a transmit pulse wave-pattern 56. The transmit signal has a pulse repetition period $T_{PR}$, and thus a pulse repetition frequency (PRF) of $f_R=1/T_{PR}$. During a portion of a given period, a pulse wave-form 82 is generated. The pulse wave-form 82 has a time duration $P_T$ and a spatial pulse length (distance) $P_l$. The wave-form 82 preferably has a constant pulse length during each pulse repetition period. The constant length is a minimum of approximately five cycles in some applications, but has a preferred length of approximately 25–30 cycles. An exemplary range is 3–60 cycles. In the example illustrated the pulse wave-form 82 has 5 cycles defining a sinusoidal pulse wave-form with a wavelength $\lambda$ and a frequency $1/T_P$. Another characteristic of the pulse wave-pattern 56 is its duty cycle. The duty cycle is the pulse duration, $P_T$, divided by the pulse repetition period, $T_{PR}$.

Figure 7:
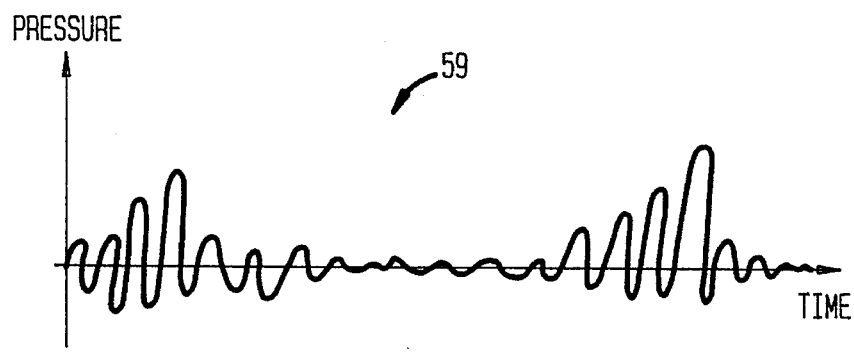
FIG. 7 is a chart of a receive signal obtained from a transducer element in response a receive beam-pattern.

As the transmit pulse wave-pattern 56 propagates through the patient anatomy, the ultrasound energy is absorbed, refracted, dispersed and reflected. The propagating refracted portions generally define the wave-pattern 56 direction 60 and path 58 (see FIG. 3). The reflected portions captured within the receive aperture 54 generally define the receive beam-pattern 66. FIG. 7 shows a receive signal 59 generated by a transducer element in response to ultrasound echoes.

The gated receiver 18 defines time windows for detecting echo responses to the transmit pulse wave-pattern 56. As described above a primary range gate 72 is defined by focusing the transmit pulse wave-pattern 56 and the receive beam-pattern 66 at the target sample volume of interest. The intersection is the primary range gate 72. As described above, secondary range gates 74 occur as artifacts during-certain applications. The sampled echoes within the primary range gate 72 and secondary range gate(s) 74 of the receive beam-pattern 66 exhibit a doppler-shift if there is motion within such gates.

Figure 8:
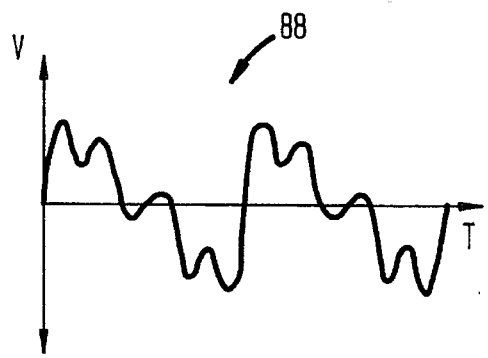
FIG. 8 is a chart of a doppler frequency signal derived from a receive signal.

FIG. 8 shows an exemplary doppler signal 88 derived from a receive beam-pattern 66 sampled over a given time interval. The signal 88 shown is a smoother filtered signal derived from discrete samples of the receive beam-pattern 66. The signal 88 depicts voltage amplitude versus time.

Note that the receive beam-pattern 66 includes several frequencies. If flow occurs within the range gates 72, 74 then doppler-shifts of the pulse wave-form frequency occur—(i.e., shifts away from frequency $1/T_P$).

Figure 9:
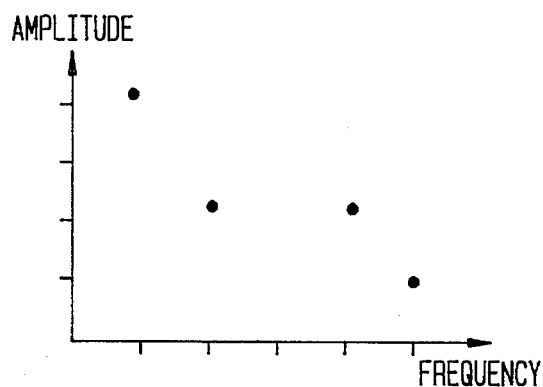
FIG. 9 is a doppler-shift frequency spectral analysis of the signal of FIG. 8.
Figure 10:
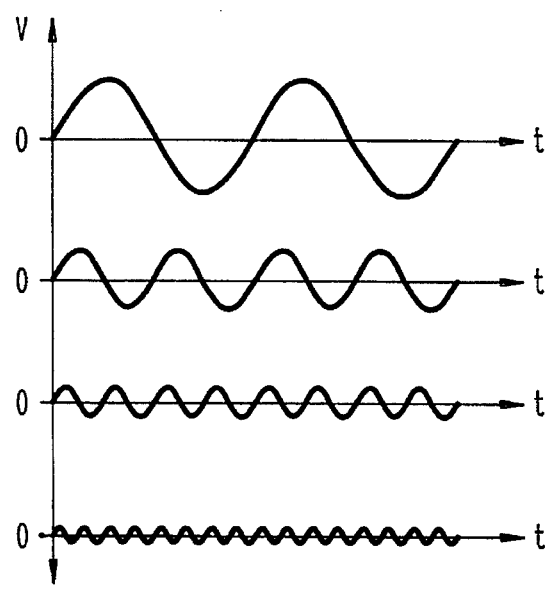
FIG. 10 is a chart of the component doppler-shift frequencies in the signal of FIG. 8.
Figure 11:
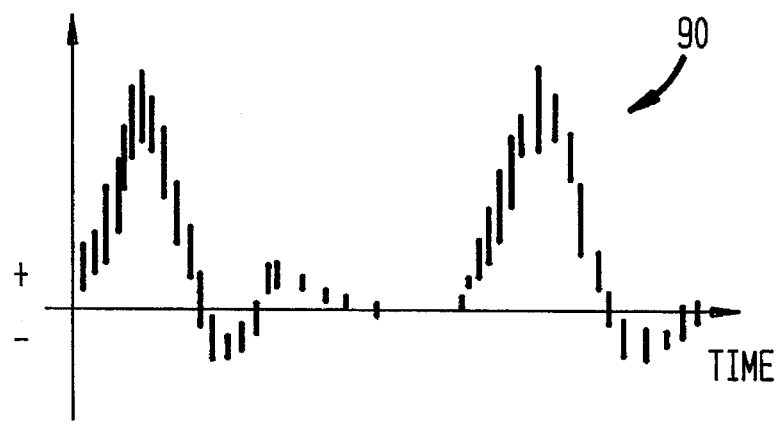
FIG. 11 is a chart of doppler-shift frequencies versus time depicting non-plug flow within a vessel.
Figure 12:
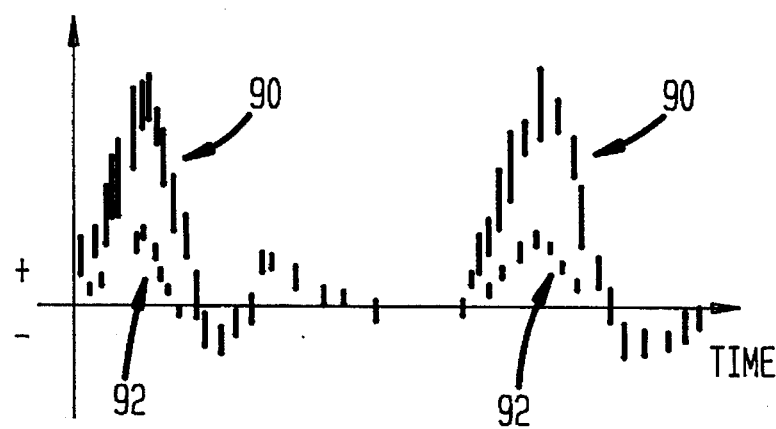
FIG. 12 is a chart the doppler-shift frequencies of FIG. 10 for a signal with range ambiguity.

FIG. 9 shows a fast Fourier transform of the derived doppler signal 88. FIG. 10 shows four component doppler-shift frequency signals making up the doppler signal 88 of FIG. 8. FIG. 11 shows a more complex doppler-shift spectra pattern 90 of doppler-shift frequencies occurring within the primary range gate 72. Such example indicates non-plug flow within a blood vessel at the target sample volume of the patient's anatomy. (Note that extraneous frequencies from secondary range gates are not present in the signal 90 of FIG. 11). FIG. 12 shows the same spectra of FIG. 11, but with range ambiguity causing another spectral pattern 92. Using the method of this invention, the spectral pattern 92 would appear at a lower brightness in a B-mode scan or would not have sufficient amplitude to be registered on the display.

Typically, doppler-shift frequency spectra have one or more component frequencies. FIG. 9 shows four component frequencies. FIG. 11 shows spectra of component frequencies at various instances in time.

MERITORIOUS AND ADVANTAGEOUS EFFECTS

One advantage of the invention is that sufficiently high pulse repetition frequencies can be used in pulsed doppler ultrasound applications to avoid frequency aliasing without introducing adverse range ambiguity in the final beam-pattern. A beneficial effect is that pulsed doppler can be used effectively over a wider range of applications and deeper sample depths to detect flow patterns.

Although a preferred embodiment of the invention has been illustrated and described, various alternatives, modifications and equivalents may be used. For example, although two secondary range gates are shown in FIGS. 3–5, fewer or more secondary range gates may occur. Further, although the transmit pulse wave-pattern 56 and receive beam-pattern 66 do not coincide, are not aligned and intersect at the target sample volume, the angle formed by the two patterns 56, 66 with respect to occurring flow directions in the patient anatomy defines a doppler angle indicative of the doppler-shift detection performance.

What is claimed is:

1. A method for determining flow velocity using pulsed-doppler ultrasound beam-forming, comprising the steps of:

generating a doppler-ultrasound transmit pulse wave-pattern at a first aperture, the transmit pulse wave-pattern having a pulse repetition frequency and a first focus, the pulse wave-pattern propagating in a first direction within a patient's anatomy at a first propagation speed to at least a desired depth, the pulse repetition frequency exceeding the propagation speed divided by twice the desired depth, wherein the transmit pulse wave-pattern is refracted, absorbed, and reflected by obstacles within the patient while propagating through the patient's anatomy, a first path of the transmit pulse wave-pattern generally defined by refracted wave-patterns;

sensing received ultrasound echoes from the patient's anatomy responsive to the transmit pulse wave-pattern at only one aperture, said only one aperture being a second aperture, said second aperture not overlapping the first aperture;

defining a receive beam-pattern from the received ultrasound echoes, the receive beam-pattern having a second focus and propagating in a second direction, the first and second directions being non-coincident, the first and second focus intersecting to define a primary range gate within which a doppler-shift frequency spectrum is sampled, and wherein a secondary range gate occurs along the receive beam-pattern away from the second focus and generally out of the first path of the transmit pulse wave-pattern; and analyzing the receive beam-pattern to define doppler-shift component frequencies, wherein non-intersection of the transmit pulse wave-pattern and secondary range gate lessens the strength of doppler-shift component frequencies sampled from the secondary range gate relative to doppler-shift component frequencies sampled from the primary range gate, and wherein said doppler-shift component frequencies are indicative of said flow velocity.

2. A pulsed-doppler ultrasound apparatus for determining flow velocity within a target area of a patient using only one transmit aperture and only one receive aperture, the apparatus comprising:

a first transducer which defines the one transmit aperture and emits a doppler-ultrasound transmit pulse wave-pattern, the pulse wave-pattern having a pulse repetition frequency and a first focus, the pulse wave-pattern propagating in a first direction within a patient's anatomy at a first propagation speed to at least a desired depth within the target area, the pulse repetition frequency exceeding the propagation speed divided by twice the desired depth;

a second transducer which defines the one receive aperture and senses a receive beam-pattern of ultrasound echoes from the patient's anatomy responsive to the transmit pulse wave-pattern, the receive beam-pattern having a second focus and propagating in a second direction, the first and second directions being non-aligned, the first and second focus intersecting to define a primary range gate within which a doppler-shift frequency spectrum is sampled, the receive aperture not overlapping the transmit aperture wherein a secondary range gate occurs along the receive beam-pattern away from the second focus and generally out of a transmit pulse wave-pattern path defined by the first direction;

a receiver which gates ultrasound echoes received at the receive aperture to define the receive beam-pattern sensed by the second transducer; and means for determining flow velocity from the sampled doppler-shift frequency spectrum.

3. The apparatus of claim 2, in which the first transducer comprises a first plurality of transducer elements and the second transducer comprises a second plurality of transducer elements, the first and second plurality comprising a transducer array.

* * * * *